US006444643B1

(12) United States Patent
Steiner et al.

(10) Patent No.: US 6,444,643 B1
(45) Date of Patent: Sep. 3, 2002

(54) METHODS OF USING INHIBITORS OF CYCLOPHILIN ROTAMASE ACTIVITY TO AFFECT NEUROLOGICAL ACTIVITY

(75) Inventors: Joseph P. Steiner, Finksburg; Gregory S. Hamilton, Catonsville; Solomon H. Snyder, Baltimore, all of MD (US)

(73) Assignees: Guilford Pharmaceuticals Inc., Baltimore, MD (US); Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/321,762

(22) Filed: May 28, 1999

Related U.S. Application Data

(63) Continuation of application No. 08/560,685, filed on Nov. 20, 1995, now abandoned.

(51) Int. Cl.[7] .......................... A61K 38/03; A61K 38/13
(52) U.S. Cl. ............................... 514/11; 514/2; 514/12
(58) Field of Search .................................. 514/2, 11–12

(56) References Cited

U.S. PATENT DOCUMENTS

| | | | | |
|---|---|---|---|---|
| 5,100,899 | A | * | 3/1992 | Calne |
| 5,321,009 | A | | 6/1994 | Baeder et al. |
| 5,330,993 | A | | 7/1994 | Armistead et al. |
| 5,614,547 | A | * | 3/1997 | Hamilton et al. |
| 5,898,029 | A | | 4/1999 | Lyons et al. |
| 6,080,753 | A | | 6/2000 | Lyons et al. |

FOREIGN PATENT DOCUMENTS

| WO | WO 96/40633 | 12/1996 |
|---|---|---|

OTHER PUBLICATIONS

Swanson, Selene K.H., et al., "Cylosporin–mediated inhibition of bovine calcineurin by cyclophilins A and B," *Biochemistry*, vol. 89, pp. 3741–3745, May 1992.

McKeon, Frank, "When Worlds Collide: Immunosuppressants Meet Protein Phosphatases," *Cell*, vol. 66, 823–826, Sep. 6, 1991.

Steiner, Joseph P., et al., "High Brain Densities of the Immunophilin FKBP colocalized with calcineurin," *Nature*, 584–587, vol. 358, Aug. 13, 1992.

Liu, Jun, et al., "Calcineurin is a Common Target of Cyclophilin–Cyclosporin A and FKBP–FK506 Complexes," *Cell*, 66(4); 807–815 (1991).

Liu, J., et al., "Inhibition of T Cell Signaling by Immunophilin–Ligand Complexes Correlates with Loss of Calcineurin Phosphatase Activity," *Biochemistry* 1992, 31, 3896–3901.

Dumont, Francis J., et al., "The Immunosuppressive Macrolides FK–506 and Rapamycin Act as Reciprocal Antagonists in Murine T Cells," *The Journal of Immunology*, vol. 144, 1418–1424, No. 4, Feb. 15, 1990.

Schreiber, Stuart L., et al., "The Mechanism of Action of Cyclosporin A and FK506," *Immunology Today*, vol. 13, No. 4, 1992.

Dawson, Ted M., et al., "Immunosuppressant FK506 Enhances Phosphorylationof Nitric Oxide Synthase and Protects Against Glutamate Neurotoxicity," *Proc. Natl. Acad. Sci. USA*, vol. 90, pp. 9808–9812, Nov. 1993.

Bredt, David S., Nitric Oxide Snthase Regulatory Sites, *J. Biol. Chem.* 267(16) 10976–81 (1992).

Dawson, Valina L., et al., "Nitric Oxide Mediates Glutamate Neurotoxicity in Primary Cortical Cultures," *Proc. Natl. Acad. Sci. USA*, vol. 88, pp. 6368–6371, Jul. 1991.

Dawson, Valina L., et al., "Mechanisms of Nitric Oxide—Mediated Neurotoxicity in Primary Brain Cultures," *The Journal of Neuroscience*, Jun. 1993, 13(6): 2651–2661.

Liu, Yuehueng, et al., "Dephosphorylation of Neuromodulin by Calcineurin," *J. Biol. Chem.* 264(22) 12800–04 (1989).

Snipes, G.J., et al., "Regulation of Specific Neuronal and Non–neuronal Proteins During Development and Following Injury in the Rat Central Nervous System," *Progress in Brain Research*, vol. 71, 155–75, F.J. Seil, E. Herbert and B.M. Carlson (Eds.), 1987.

Benowitz, Larry I., et al., "A Membrane Phosphoprotein Associated with Neural Development, Axonal Regeneration, Phospholipid Metabolism, and Synaptic Plasticity," *TINS*, vol. 10, No. 12, 1987.

Skene, J.H. Pate, "Axonal Growth–Associated Protein," *Ann. Rep. Neurosci.* 1989, 12:127–56.

Tetzlaff, W., et al., "Axonal Transport and Localization of B–50/GAP–43–like Immunoreactivity in Regenerating Sciatic and Facial Nerves of the Rat," *The Journal of Neuroscience*, Apr. 1989, 9(4), 1303–1313.

Greene, Lloyd A., et al., "Establishment of a Noradrenergic Clonal Line of Rat Adrenal Pheochromocytoma Cells Which Respond to Nerve Growth Factor," *Proc. Natl. Acad. Sci. USA*, vol. 73, No. 7, pp. 2424–2428, Jul. 1976.

Yankner, Bruce A., et al., "Transfection of PC12 Cells with the Human GAP–43 Gene: Effects on Neurite Outgrowth and Regeneration," *Molecular Brain Research*, 7 (1990) 39–44.

(List continued on next page.)

Primary Examiner—Gary L. Kunz
Assistant Examiner—Stephen Gucker
(74) Attorney, Agent, or Firm—Howrey Simon Arnold & White, LLP

(57) ABSTRACT

This invention relates to the method of using neurotrophic cyclophilin inhibitor compounds having an affinity for cyclophilin-type immunophilins as inhibitors of the enzyme activity associated with immunophilin proteins, and particularly inhibitors of peptidyl-prolyl isomerase or rotamase enzyme activity.

6 Claims, 1 Drawing Sheet

OTHER PUBLICATIONS

Bierer, Barbara E., "Two Distinct Signal Transmission Pathways in T Lymphocytes are Inhibited by Complexes Formed Between an Immunophilin and Either FK506 or Rapamycin," *Proc. Natl. Acad. Sci. USA*, vol. 87, pp. 9231–9235, Dec. 1990.

Calvo, Victor, et al., "Interleukin 2 Stimulation of p70 S6 Kinase Activity is Inhibited by the Immunosuppressant Rapamycin,"*Proc. Natl. Acad. Sci. USA*, vol. 89, pp. 7571–7575, Aug. 1992.

Chung, Jongkyeong, et al., "Rapamycin–FKBP Specifically Blocks Growth–Dependent Activation of and Signaling by the 70 kd S6 Protein Kinases," *Cell*, vol. 69, 1227–1236, Jun. 26, 1992.

Kuo, Calvin J., "Rapamycin Selectively Inhibits Interleukin–2 Activation of p70 S6 Kinase," *Nature*, vol. 358, 70–73, Jul. 2, 1992.

Kunz, Jeannette, et al., "Target of Rapamycin in Yeast, TOR2, Is an Essential Phosphatidylinositol Kinase Homolog Required for G1 Progression," *Cell*, vol. 73, 585–596, May 7, 1993.

Jin, Yong Jiu, et al., "The 25–kDa FK506–binding Protein is Localized in the Nucleus and Associates with Casein Kinase II and Nucleolin," *Proc. Natl. Acad. Sci. USA*, vol. 90, pp. 7769–7773, Aug. 1993.

Ferrari, Stefano, et al., The Immunosuppressant Rapamycin Induces Inactivation of $p70^{s6k}$ through Dephosphorylation of a Novel Set of Sites, *The Journal of Biological Chemistry*, vol. 268, No. 22, pp. 16091–16094, Aug. 5, 1993.

Schreiber, Stuart L., "Chemistry and Biology of the Immunophilins and Their Immunosuppressive Ligands," *Science*, vol. 251, 283–287, Jan. 18, 1991.

Dumont, Francis J., et al., "Distinct Mechanisms of Suppression of Murine T Cell Activation by the Related Macrolides FK–506 and Rapamycin," *The Journal of Immunology*, vol. 144, 251–258, No. 1, Jan. 1, 1990.

Thoenen, H., et al., "Physiology of Nerve Growth Factor," *Physiological Reviews*, vol. 60, No. 4, 1284–1335, Oct. 1980.

DeFranco, Anthony L., "Immunosuppressants at Work," *Nature*, vol. 352, 754–55, Aug. 29, 1991.

Matsuoka, Ichiro, et al., "Cell–Type specific Regulation of Nerve Growth Factor (NGF) Synthesis in Non–Neuronal Cells: Comparison of Schwann Cells with Other Cell Types," *The Journal of Neuroscience*, Oct. 1991, 11(10): 3165–3177.

Levi, A., et al., "The Mode of Action of Nerve Growth Factor in PC12 Cells," *Molecular Neurobiology*, vol. 2, 201–26, 1988.

Fujita, Ko, et al., "Regulation of the Differentiation of PC12 Pheochromocytoma Cells," *Environmental Health Perspectives*, vol. 80, pp. 127–142, 1989.

Mehta, Sujata, et al., "Neurite Outgrowth and Protein Phosphorylation in Chick Embryonic Sensory Ganglia Induced by a Brief Exposure to 12–O–Tetradecanoylphorbol 13–Acetate," *Journal of Neurochemistry*, vol. 60, No. 3, 972–81, 1993.

Hsu, Linda, "the Effect of 12–O–Tetradecanoylphorbol–13–Acetate (TPA) on Axonal Elongation and Fasciculation," *Anatomy and Embryology*, 1989, 179:511–518.

Hashimoto, Seiichi, et al., "Blockage of Nerve Growth Factor Action in PC12h Cells by Staurosporine, a Potent Protein Kinase Inhibitor," *Journal of Neurochemistry*, vol. 53, No. 6, 1675–85, 1989.

Bixby, John L., "Protein Kinase C Is Involved in Laminin Stimulation of Neurite Outgrowth," *Neuron* 3(3):287–97 (1989).

Morrison, Richard S., et al., "Inhibition of Protein Kinase C Activity Promotes the Neurotrophic Actionof Epidermal and Basic Fibroblast Growth Factors," *Brain Research*, 473 (1988) 141–146.

Mattson, M. P., et al., "Intracellular Messengers in the Generation and Degeneration of Hippocampal Neuroarchitecture," *Journal of Neuroscience Research*, 21:447–464 (1988).

Girard, Peggy R., et al., "Protein Inase C and Its 80–Kilodalton Substrate Protein in Neuroblastoma Cell Neurite Outgrowth," *Journal of Neurochemistry*, vol. 54, No. 1, 300–306, 1990.

Reinhold, David, et al., "The Lack of a Role for Protein Kinase C in Neurite Extension and in the Induction of Ornithine Decarboxylase by Nerve Growth Factor in PC12 Cells," *J. Biol. Chem.* 264(6): 3538–44 (1989).

Baetge, E. Edward, et al., "Neurite Outgrowth in PC12 Cells Deficient in GAP–43," *Neuron*, vol. 6, 21–30, Jan. 1991.

Meiri, Karina F., et al., "Monoclonal Antibodies Show That Kinase C. Phosphorylation of GAP–43 during Axonogenesis Is Both Spatially and Temporally Restricted In Vivo," *The Journal of Cell Biology*, vol. 112, No. 5, 991–1005, Mar. 1991.

Jayaraman, Thottala, et al., "FK506 Binding Protein Associated with the Calcium Release Channel (Ryanodine Receptor)", *The Journal of Biological Chemistry*, vol. 267, No. 14, pp. 9474–9477, May 15, 1992.

Timerman, Anthony P., et al., "The Calcium Release Channel of Sarcoplasmic Reticulum is Modulated by FK–506–binding Protein," *The Journal of Biological Chemistry*, 268 (31): 22992–9 (1993).

Galat, Andrzej, et al., "A Rapamycin–Selective 25–kDa Immunophilin," *Biochemistry*, vol. 31, No. 8, 1992.

Jin, Yong–Jiu, et al., "Molecular Cloning of a 25–kDa High Affinity Rapamycin Binding Protein, FKBP25," *The Journal of Biological Chemistry*, vol. 267, No. 16, pp. 10942–10945, Jun. 5, 1992.

Tai, Ping–Kaung Ku, et al., "Association of a 59–Kilodalton Immunophilin with the Glucocorticoid Receptor Complex," *Science*, vol. 256, 1315–18, May 29, 1992.

Yem, Anthony W., et al., "The Hsp56 Component of Steroid Receptor Complexes Binds to Immobilized FK506 and Shows Homology to FKBP–12 and FKBP–13," *The Journal of Biological Chemistry*, vol. 267, No. 5, pp. 2868–2871, Feb. 15, 1992.

Jin, Yong–Jiu, et al., "Molecular Cloning of a Membrane–Associated Human FK506– and Rapamycin–binding Protein, FKBP–13," *Proc. Natl. Acad. Sci. USA*, vol. 88, pp. 6677–6681, Aug. 1991.

Phelps, C.H., et al., "Commentary: Potential Use of Nerve Growth Factor to Treat Alzheimer's Disease," *Neurobiology of Aging*, vol. 10, pp. 205–207, 1989.

Tetzlaff, Wolfram, et al., "Response of Facial and Rubrospinal Neurons to Axotomy: Changesin mRNA Expression for Cytoskeletal Proteins and GAP–43," *The Journal of Neuroscience*, Aug. 1991, 11(8): 2528–2544.

Maki, Noboru, et al., "Complementary DNA Encoding the Human T–Cell FK506–binding Protein, A Peptidylprolyl cis–trans Isomerase Distinct from Cyclophilin," *Proc. Natl. Acad. Sci. USA*, vol. 87, pp. 5440–5443, Jul. 1990.

Standaert, Robert F., et al., "Molecular Cloning and Overexpression of the Human FK–506–binding Protein FKBP," *Nature*, vol. 346, 671–674, Aug. 16, 1990.

Rosenthal, A., et al., "Primary Structure and mRNA Localization of Protein F1, A Growth–Related Protein Kinase C Substrate Associated with Synaptic Plasticity," *The EMBO Journal*, vol. 6, No. 12, pp. 3641–3646, 1987.

Ito, Akira, et al., "The Complete Primary Structure of Calcineurin A, A Calmodulin Binding Protein Homologous with Protein Phosphatases 1 and 2A," *Biochemical and Biophysical Research Communications*, vol. 163, No. 3, pp. 1492–1497, 1989.

Kuno, Takayoshi, et al., "Evidence for a Second Isoform of the Catalytic Subunit of Calmodulin–Dependent Protein Phosphatase (Calcineurin A)," *Biochemical and Biophysical Reserach Communications*, vol. 165, No. 3, pp. 1352–1358, 1989.

Saika, Takanori, et al., "Effects of Nerve Crush and Transection on mRNA Levels for Nerve Growth Factor Receptor in the Rat Facial Motoneurons," *Molecular Brain Research*, 9 (1991) 157–160.

Bisby, M.A., "Dependence of GAP43 (B50, F1) Transport on Axonal Regeneration in Rat Dorsal Root Ganglion Neurons," *Brain Research*, 458 (1988) 157–161.

Hoffman, Paul N., "Expression of GAP–43, a Rapidly Transported Growth–Associated Protein, and Class II Beta Tubulin, a Slowly Transported Cytoskeletal Protein, are Coordinated in Regenerating Neurons," *The Journal of Neuroscience*, 893–97, Mar. 1989, 9(3).

Sommervaille, T., et al., "Time–Dependent Difference in the Increase in GAP–43 Expression in Dorsal Root Ganglion Cells After Peripheral Axotomy," *Neuroscience*, vol. 45, No. 1, pp. 213–220, 1991.

Van der Zee, Catharina E.E.M., et al., "Expression of Growth–Associated Protein B–50 (GAP43) in Dorsal Root Ganglia and Sciatic Nerve During Regenerative Sprouting," *The Journal of Neuroscience*, Oct. 1989, 9(10), 3505–3512.

Verge, V.M.K., et al., "Correlation Between GAP43 and Nerve Growth Factor Receptors in Rat Sensory Neurons," *The Journal of Neuroscience*, Mar. 1990, 10(3), 926–934.

Schreyer, David J., et al., "Fate of GAP–43 in Ascending Spinal Axons of DRG Neurons After Peripheral Nerve Injury: Delayed Accumulation and Correlation with Generative Potential," *The Journal of Neuroscience*, Dec. 1991, 11(2), 3738–3751.

Woolf, C.J., et al., "The Growth–Associated Protein GAP–43 Appears in Dorsal Root Ganlgion Cells and in the Dorsal Horn of the Rat Spinal Cord Following Peripheral Nerve Injury," *Neuroscience* 34(2): 465–78 (1990).

Chong, M.S., et al., "GAP–43 mRNA in Rat Spinal Cord and Dorsal Root Ganglia Neurons: Development Changes and Re–expression Following Peripheral Nerve Injury," *European Journal of Neuroscience*, vol. 4, pp. 83–895, 1992.

Basi, Guriqbal S., et al., "Primary Structure and Transcriptional Regulation of GAP–43, a Protein Associated with Nerve Growth," *Cell*, vol. 49, 785–791, Jun. 19, 1987.

Wiese, U.H., et al., "Differential Expression of Growth–Associated Protein (GAP–43) mRNA in Rat Primary Sensory Neurons After Peripheral Nerve Lesion: A Non–Radioactive In Situ Hybridisation Study," *Brain Res.* 592:141–56 (1992).

Streit, Wolfgang J., et al., "Response of Endogenous Glial Cells to Motor Neuron Degeneration Induced by Toxic Ricin," *The Journal of Comparative Neurology*, 268:248–263 (1988).

Skene, J.H. Pate, et al., "Changes in Axonally Transported Proteins During Axon Regeneration in Toad Retinal Ganglion Cells," *The Journal of Cell Biology*, vol. 89, Apr. 1981, 86–95.

Skene, J.H. Pate, et al., "Axonally Transported Proteins Associated with Axon Growth in Rabbit Central and Peripheral Nervous Systems," *The Journal of Cell Biology*, vol. 89, Apr. 1981, 96–103.

Grafstein, Bernice, et al., "Intracellular Transport in Neurons," *Physiological Reviews*, vol. 60, No. 4, 1167–1283, Oct. 1980.

Lieberman, A.R., "The Axon Reaction: A Review of the Principal Features of Perikaryal Responses to Axon Injury," *Int. Rev. Neurobiol.* 14:49–124 (1971).

Lyons, W. Ernest, et al., "Immunosuppressant FK506 Promotes Neurite Outgrowth in Cultures of PC12 Cells and Sensory Ganglia," *Proc. Natl. Acad. Sci. USA*, vol. 91, pp. 3191–3195, Apr. 1994.

Tindall, Richard S.A., "Immunointervention with Cyclosporin A in Autoimmune Neurological Disorders," *Journal Autoimmun.* 1992 Apr., 5 Suppl. A: 301–13.

Ryba, M., et al., "Cyclosporine A Prevents Neurological Deterioration of Patients with SAH—A Preliminary Report," *Acta Neurochir.* (Wien) (1991) 112:25–27.

Kitamura, Yoshihisa, et al., "Suppressive Effect of FK–506, A Novel Immunosuppressant, Against MPTP–Induced Dopamine Depletion in the Striatum of Young C57BL/6 Mice," *Journal of Neuroimmunology*, 50 (1994) 221–224.

Shiga, Yusei, et al., "Cyclosporin A Protects Against Ischemia–Reperfusion Injury in the Brain," *Brain Research*, 595 (1992) 145–148.

Teichner, Angela, et al., "Treatment with Cyclosporine A Promotes Axonal Regeneration in Rats Submitted to Transverse Section of the Spinal Cord," *Journal fur Hirnforschung*, 34 (1993)3, 343–349.

Steiner, Joseph P., et al., "Neurotrophic Actions of Nonimmunosuppressive Analogues of Immunosuppressive Drugs FK506, Rapamycin and Cyclosporin A," *Nature Medicine*, vol. 3, 421–28, Apr. 1997.

Steiner, Joseph P., et al., "Neurotrophic Immunophilin Ligands Stimulate Structural and Functional Recovery in Neurodegenerative Animal Models," *Proc. Natl. Acad. Sci. USA*, vol. 94, pp. 2019–2024, Mar. 1997.

Sharkey, John, et al., "Immunophilins Mediate the Neuroprotective Effects of FK506 in Focal Cerebral Ischaemia," *Nature*, vol. 371, 336–39, Sep. 22, 1994.

Gold, Bruce G., et al., "The Immunosuppressant FK506 Increases Functional Recovery and Nerve Regeneration Following Peripheral Nerve Injury," *Restorative Neurology and Neuroscience*, 6 (1994) 287–296.

Wiley, Ronald G., et al., "Suicide Transport: Destruction of Neurons by Retrograde Transport of Ricin, Abrin, and Modeccin," *Science*, vol. 216:889–890, May 1982.

Handschumacher, Robert E., et al., "Cyclophilin: A Specific Cytosolic Binding Protein for Cyclosporin A," *Science*, vol. 226:554–546, Nov. 1984.

Price, D.J., et al., "Rapamycin–Induced Inhibition of the 70–Kilodalton S6 Protein Kinase," *Science*, vol. 257:973–977, Aug. 1992.

Fruman, David A., et al., "Calcineurin phosphatase activity in T lymphocytes is inhibited by FK 506 and cyclosporin A," *Proc. Natl. Acad. Sci. USA* 89 (1992) 3686–3690.

\* cited by examiner

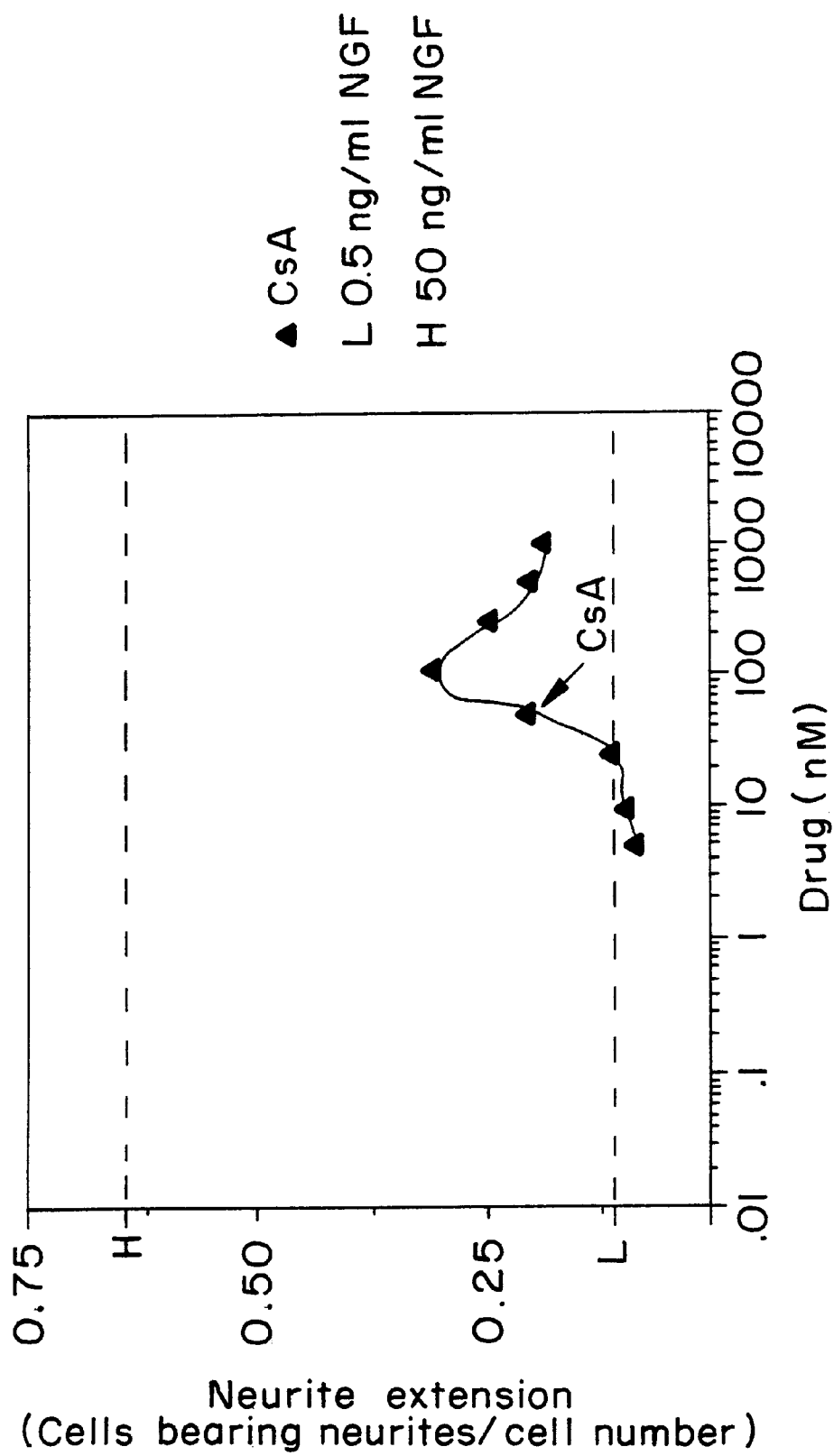

METHODS OF USING INHIBITORS OF CYCLOPHILIN ROTAMASE ACTIVITY TO AFFECT NEUROLOGICAL ACTIVITY

This application is a continuation of U.S. Ser. No. 08/560,685, filed Nov. 20, 1995 now abandoned, entitled "INHIBITORS OF CYCLOPHILIN ROTAMASE ACTIVITY".

FIELD OF THE INVENTION

This invention relates to the method of using neurotrophic cyclophilin inhibitor compounds having an affinity for cyclophilin immunophilins as inhibitors of the enzyme activity associated with immunophilin proteins, and particularly inhibitors of peptidyl-prolyl isomerase or rotamase enzyme activity of the cyclophilins.

DESCRIPTION OF THE PRIOR ART

The term immunophilin refers to a number of proteins that serve as receptors for the principal immunosuppressant drugs, cyclosporin A (CsA), FK506, and rapamycin. Known classes of immunophilins are cyclophilins, and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

Immunophilins were originally discovered and studied in immune tissue. It was initially postulated by those skilled in the art that inhibition of the immunophilins rotamase activity leads to the inhibition of T-cell proliferation, thereby causing the immunosuppressive action exhibited by immunosuppressive drugs such as cyclosporin A, FK506, and rapamycin. Further study has shown that the inhibition of rotamase activity, in and of itself, is not sufficient for immunosuppressant activity. Instead immunosuppression appears to stem from the formulation of a complex of immunosuppressant drugs and immunophilins. It has been shown that the immunophilin-drug complexes interact with ternary protein targets as their mode of action. In the case of FKBP-FK506 and FKBP-CsA, the drug-immunophilin complexes bind to the enzyme calcineurin, inhibiting T-cell receptor signalling leading to T-cell proliferation. Similarly, the complex of rapamycin and FKBP interacts with the RAFT1/FRAP protein and inhibits signalling from the IL-2 receptor.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release, and neuronal process extension.

Surprisingly, it has been found that picomolar concentrations of an immunosuppressant such as cyclosporin A stimulates neurite out growth in PC12 cells and sensory neurons, namely dorsal root ganglion cells (DRGS). More particularly, it has been found that drugs with a high affinity for cyclophilin are potent rotamase inhibitors and exhibit excellent neurotrophic effects. Snyder et al., "Immunophilins and the Nervous System", *Nature Medicine*, Volume 1, No. 1, Jan. 1995, 32–37. These findings suggest the use of inhibitors of cyclophilin rotamase activity in treating various peripheral neuropathies and enhancing neuronal regrowth in the central nervous system (CNS). Studies have demonstrated that neurodegenerative disorders such as Alzheimer's disease and Parkinson's disease may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat SDAT patients with exogenous nerve growth factor or other neurotrophic proteins such as brain derived growth factor, glial derived growth factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentiially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321: 1725).

The present invention provides both immunosuppressive and non-immunosuppressive cyclophilin inhibitor compounds containing small molecule cyclophilin rotamase inhibitors which are extremely potent in augmenting neurite outgrowth, and for promoting and stimulating neuronal growth and regeneration in various neuropathological situations where neuronal repair can be facilitated. These situations include augmenting neurite outgrowth and promoting neuronal growth and regeneration for nerve damage by physical injury or disease state such as diabetes, including peripheral nerve damage, damage to motor neurons, damage to the central nervous system (spinal cord and brain) including damage to spinal neurons and neurons in the brain, brain damage associated with stroke, and for the treatment of neurological disorders relating to neurodegeneration, including Parkinson's disease and Alzheimer's disease.

SUMMARY OF THE INVENTION

This invention relates to the method of using. neurotrophic cyclophilin inhibitor compounds having an affinity for cyclophilin-type immunophilins as inhibitors of the enzyme activity associated with immunophilin proteins, and particularly inhibitors of peptidyl-prolyl isomerase or rotamase enzyme activity.

A preferred embodiment of this invention is a method of treating a neurological activity in an animal, comprising:
administering to an animal an effective amount of an immunosuppressive cyclosporin represented by formula I and pharmaceutically acceptable salts thereof, wherein:
$R^1$ is MeBmt or [3-DesoxyMeBmt] or represented by formula III; wherein positions 2, 3, and 4 have the configurations S, R and R, respectively;
wherein —X—Y— is connected by a double bond or a single bond; wherein:

R² is independently selected from the group consisting of Abu, Ala, Thr, Val, and norVal; R³ is Sar; R⁴ is MeLeu; R⁵ is Val; R⁶ is MeLeu; R⁷ is Ala; R⁸ is D-Ala; R⁹ is MeLeu; R¹⁰ is MeLeu; and, R¹¹ is Val or [D-MeVal].

Another preferred embodiment of this invention is a method of treating a neurological activity in an animal, comprising:
  administering to an animal an effective amount of a non-immunosuppressive cyclosporin of formula IV: wherein:
    R1 is MeBmt or dihydro MeBmt or represented by formula III; wherein positions 2, 3, and 4 have the configurations S, R and R, respectively;
    wherein —X—Y— is connected by a double bond or a single bond; wherein: $R^2$ is Abu or a fluorinated analog thereof; $R^3$ is Sar, D-MeAla, or a fluorinated analog thereof; $R^4$ is an N-methylated amino acid residue with a (C1–C9) straight or branched chain alkyl or alkenyl group;. these straight or branched alkyl or alkenyl groups may be substituted by cycloalkyl (C3–C8); $R_1$ may also be (C3–C8) cycloalkyl or (C5–C7) cycloalkenyl;
    the above alkyl, alkenyl, cycloalkyl or cycloalkenyl groups may be substituted with (C1–C4) alkyl or (C1–C4) alkenyl, or hydroxy, especially where $R^4$ is MeLeu, MeVal, Me homo-Ala, or [Me-(α-methyl) Thr]; $R^5$ is Val or a fluorinated analog thereof; $R^6$ is MeAla, MeAbu, or a fluorinated analog thereof; $R^7$ is Ala or a fluorinated derivative thereof; $R^8$ is (a) D-Ala or a fluorinated analog thereof; or (b) O-acyl-D-Ser or O-acyl-D-Thr wherein the acyl group is defined as $R^{12}$—CO— where $R^{12}$ represents hydrogen, $C_{1-6}$alkyl, phenyl or substituted phenyl of formula V wherein $X^1$ and $X^2$ independently are (a) $C_{1-6}$alkyl;
    (b) $C_{1-6}$alkanoyl; (c) $CH_2OH$; (d) halo; (e) $C_{1-6}$alkoxy; (f) —$NH_2$; (g) —$NO_2$; (h) —COOH; (i) —$COOC_{1-6}$alkyl; or (j) —H; $R^9$ and $R^{10}$ are independently MeLeu or a fluorinated analog thereof; and, $R^{11}$ is MeVal or a fluorinated analog thereof.

Another preferred embodiment of this invention is a method of treating a neurological disorder in an animal, comprising: administering to an animal an effective amount of a cyclophilin inhibitor having an affinity for cyclophilin-type immunophilins to stimulate growth of damaged peripheral nerves or to promote neuronal regeneration, wherein the cyclophilin-type immunophilin exhibits rotamase activity and the cyclosporin derivative inhibits said rotamase activity of the immunophilin.

Another preferred embodiment of this invention is a method of treating a neurological disorder in an animal, comprising:
  administering to an animal an effective amount of a cyclophilin inhibitor having an affinity for cyclophilin-type immunophilins in combination with an effective amount of a neurotrophic factor selected from the group consisting of neurotrophic growth factor, brain derived growth factor, glial derived growth factor, cilial neurotrophic factor, and neurotropin-3, to stimulate growth of damaged peripheral nerves or to promote neuronal regeneration, wherein the cyclophilin-type immunophilin exhibits rotamase activity and the cyclosporin derivative inhibits said rotamase activity of the immunophilin.

Another preferred embodiment of this invention is a method of stimulating growth of damaged peripheral nerves, comprising; administering to damaged peripheral nerves an effective amount of a cyclophilin inhibitor compound having an affinity for cyclophilin-type immunophilins to stimulate or promote growth of the damaged peripheral nerves, wherein the cyclophilin-type immunophilins exhibit rotamase activity and the cyclosporin derivative inhibits said rotamase activity of the immunophilin.

Another preferred embodiment of this invention is a method of stimulating growth of damaged peripheral nerves, comprising:
  administering to damaged peripheral nerves an effective amount of an FKBP inhibitor compound having an affinity for cyclophilin-type immunophilins to stimulate growth of damaged peripheral nerves, wherein the cyclophilin-type immunophilin exhibit rotamase activity and the cyclosporin derivative inhibits said rotamase activity of the immunophilin.

Another preferred embodiment of this invention is a method for promoting neuronal regeneration and growth in animals, comprising:
  administering to an animal an effective amount of a cyclophilin inhibitor compound having an affinity for cyclophilin-type immunophilins to promote neuronal regeneration, wherein the cyclophilin-type immunophilins exhibit rotamase activity and the cyclosporin derivative inhibits said rotamase activity of the immunophilin.

Yet another preferred embodiment of this invention is a method for preventing neurodegeneration in an animal, comprising:
  administering to an animal an effective amount of a cyclophilin inhibitor having an affinity for cyclophilin-type immunophilins to prevent neurodegeneration, wherein the cyclophilin-type immunophilin exhibits rotamase activity and the cyclosporin derivative inhibits said rotamase activity of the immunophilin.

BRIEF DESCRIPTION OF THE DRAWINGS

FIG. 1 is dose-response curve for Cyclosporin A. FIG. 1 shows a typical dose at which $ED_{50}$ for CsA, the dose at which 50% of the maximal response was elicited, is calculated to be 50 nM.

DETAILED DESCRIPTION OF THE INVENTION

The novel neurotrophic cyclophilin inhibitor compounds f this invention have an affinity for the cyclosporin binding protein, cyclophilin. When the neurotrophic compounds of the invention are bound to cyclophilin, they have been found to inhibit the prolyl-peptidyl cis-trans isomerase activity, or rotamase activity of the binding protein and unexpectedly stimulate neurite growth.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalensulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention are potent inhibitors of rotamase activity and possess an excellent degree of neurotrophic activity. This activity is useful in the stimulation of damaged neurons, the promotion of neuronal regeneration, the prevention of neurodegeneration, the stimulation of growth of damaged peripheral nerves, the stimulation of growth of damaged neurons in the spinal cord, the stimulation of growth of motor nerves, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, progressive muscular atrophy, progressive bulbar inherited muscular atrophy, herniated, ruptured or prolapsed invertabrae disk syndromes, cervical spondylosis, plexus disorders, thoracic outlet destruction syndromes, peripheral neuropathic such as those caused by lead, dapsone, ticks, porphyria, or Gullain-Barré syndrome, Alzheimer's disease, and Parkinson's disease.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets the immunophilin-drug complex should readily penetrate the blood-brain barrier when peripherally administered. Compounds of this invention which cannot penetrate the blood-brain barrier can be effectively administered by an intraventricular route.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

Methods and Procedures
Nerve Extension Elicited in Chick Dorsal Root Ganglia by Cyclophilin Ligands In the present study we have employed explants of chick dorsal root ganglia in order to demonstrate the powerful neurotrophic effects of the cyclophilin binding compounds. The maximal increase in the number of processes, their length and branching is quite similar at maximally effective contractions of the cyclophilin ligands and of NGF (100 ng/ml). With progressively increasing concentrations of the various drugs, one observes a larger number of processes, more extensive branching and a greater length of individual processes.

We evaluated the potencies of drugs in binding to cyclophilin A by examining inhibition of peptidyl prolylisomerase activity (Table 1). There is a striking parallel between their potencies in stimulating neurite outgrowth and inhibiting rotamase activity.

The very close correlation between the potencies of drugs in binding to immunophilins, inhibiting their rotamase activity and stimulating neurite outgrowth implies that inhibition of rotamase activity is responsible for neurotrophic effects of the drugs. The extraordinarily high potency of the drugs in stimulating neurite outgrowth and in binding to cyclophilin makes it most unlikely that any other target could account for the neurotrophic effects.

Because of the extraordinary potency of the drugs and the close correlation between rotamase inhibition and neurotrophic actions, we conclude that rotamase inhibition of cyclophilin is likely involved in neurotrophic effects.

The neurotrophic actions of the drugs studied here are exerted at extremely low concentrations indicating potencies comparable to those of neurotrophic proteins such as brain derived growth factor, neurotropin-3 and neurotrophic growth factor.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

Illustrative cyclophilin inhibitor compounds which can be used for the purposes of this invention include, but are not limited to, the following. Cyclosproins of general structural Formula I, comprising cyclic peptides which contain 11 amino acids:

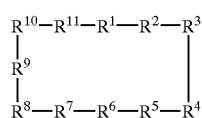

Formula I

More Particularly, naturally occurring cyclosporins have the general structure shown in Formula II and embodied in the present invention:

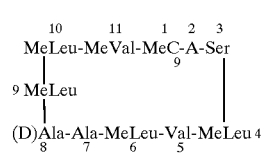

Formula II wherein "MeC$_9$" represents the so-called "C9-amino acid" residue of Formula III (also known as "MeBmt" =(4R)-4-[(E)-2-butenyl]-4-methyl-L-threonine):

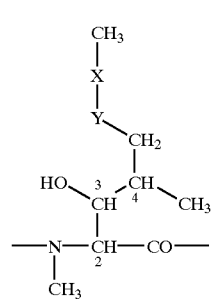

Formula III in which positions 2, 3, and 4 have the configurations S, R and R, respectively, —X—Y— is —CH=CH— (trans; where Me=methyl Abu=a-aminobutyric acid Val=valine norVal=norvaline Ala=alanine MeLeu=N-methyl-leucine MeVal=N-methyl-valine Sar=sarcosine

[3-DesoxyMeBmt]=MeBmt wherein the oxygen at position 3 is removed.

Unless specified, the amino acid configuration is L; and A is, for cyclosporin A, -Abu-;

for cyclosporin B, -Ala-;

for cyclosporin C, -Thr-;

for cyclosporin D, -Val-; and for cyclosporin G, -norVal-, all of which are incorporated herein by reference. Additional known naturally ocurring cyclosporins are related to cyclosporin A, above, by replacement of an amino acid; thus for cyclosporin E, position 11 is Val;

for cyclosporin F, position 1 is [3-DesoxyMeBmt]; and for cyclosporin H, position 11 is [D-MeVal], all of which are incorporated herein by reference.

In the following discussion, all references to numbered positions in the cyclosporin type structure are with reference to formula II. As is common in the field, a specific cyclosporin analog may be named using the above numbering system, using a shorthand notation to identify how the cyclosporin analog differs from cyclosporin A (CsA). Thus, [MeVal]$^4$-CsA denotes the cyclosporin in which MeLeu in cyclosporin A (Formula II) has been replaced by MeVal, and so forth.

In the case of the dihydrocyclosporins, —X—Y— of formula III is —CH$_2$—CH$_2$—. Thus, dihydrocyclosporin A, dihydrocyclosporin C and all other dihydro analogues of naturally occurring as well as semi-synthetic and synthetic cyclosporins are to be understood as falling within the spirit and scope of the invention.

In addition to these known cyclosporins and their dihydro derivatives, a number of non-natural cyclosporins have been prepared by synthetic means, either by total synthesis or synthetic modification of naturally ocurring materials, or by modified culture techniques. These synthetic and semi-synthetic cyclosporin analogues and derivatives have been shown to potently inhibit the rotamase activity of cyclophilin, and are thus to be understood as specifically falling within the scope and spirit of the present invention. Such modified cyclosporins include, but are not in any way limited to, the following:

cyclosporins with modified "C9 amino acids"; such modified cyclosporins are disclosed by Witzel (U.S. Pat. No. 4,885,276 and U.S. Pat. No. 4,798,823), and are incorporated herein by reference;

cyclosporins with modified residues at position 8, such as [dehydro-Ala]8-CsA and cyclosporins containing a sulfur-containing amino acid at position-8, as disclosed by Patchett et al. (U.S. Pat. Nos. 5,122,511 and 5,214,130) and incorporated herein by reference;

cyclosporins wherein the amino acid at the 8-position is a (D)-acyloxy-a-amino acid residue, as disclosed by Wenger (U.S. Pat. No. 4,764,503) and incorporated herein by reference;

cyclosporins having an a-hydroxycarboxylic acid at position-8, as described by Dreyfuss et al. (U.S. Pat. No. 5,116,816) and incorporated herein by reference;

cyclosporins containing hydroxy-substituted serine residue at position-8, such as [O-(2-hydroxyethyl) (D) Ser]$^8$-CsA, are disclosed by Eberle in U.S. Pat. No. 5,284,826 and incorporated herein by reference;

cyclosporins containing one or more fluorinated amino acids, as for example described by Durette et al. in U.S. Pat. No. 5,227,467 and incorporated herein by reference;

cyclosporins which contain at the 3-position an optically active, N-methylated a-amino acid residue of the (D) configuration, as disclosed by Seebach in U.S. Pat. No. 4,703,033 and incorporated herein by reference;

cyclosporins which contain an allyl-Gly residue in the 2-position and/or a —(D)—Ser residue in the 8-position, as disclosed by Bollinger et al. (U.S. Pat. No. 4,384,996) and incorporated herein by reference.

In addition to the above cyclosporins and cyclosporin analogs which possess cyclophilin inhibitory and immunosuppressive activity, it is also an intention of the present invention to provide a method for the use of non-immunosuppressive cyclosporin analogs as neurotrophic agents. Such non-immunosuppressive cyclosporin analogs bind to cyclophilin and inhibit its rotamase activity, while not eliciting immunosuppression, and are potent neurotrophic agents.

The following structural Formula IV is illustrative of such embodiment, and is not meant to be construed as limiting the scope of the invention in any way:

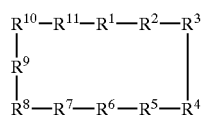

Formula IV wherein
R$^1$ is MeBmt or dihydro MeBmt;
R$^2$ is Abu or a fluorinated analog thereof;
R$^3$ is Sar, D-MeAla, or a fluorinated analog thereof;
R$^4$ is an N-methylated amino acid residue with a (C1–C9) straight or branched chain alkyl or alkenyl group; these straight or branched alkyl or alkenyl groups may be substituted by cycloalkyl (C3–C8); R$_1$ may also be (C3–C8) cycloalkyl or (C5–C7) cycloalkenyl; the above alkyl, alkenyl, cycloalkyl or cycloalkenyl groups may be substituted with (C1–C4) alkyl or (C1–C4) alkenyl, or hydroxy;
R$^9$ and R$^{10}$ are independently MeLeu or a fluorinated analog thereof;
R$^5$ is Val or a fluorinated analog thereof;
R$^6$ is MeAla, MeAbu, or a fluorinated analog thereof;
R$^7$ is Ala or a fluorinated derivative thereof;
R$^8$ is
 (a) D-Ala or a fluorinated analog thereof; or
 (b) O-acyl-D-Ser or O-acyl-D-Thr wherein the acyl group is defined as R$^{12}$—CO— where R$^{12}$ represents hydrogen, C$_{1-6}$alkyl, phenyl or substituted phenyl of formula V:

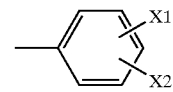

wherein X$^1$ and X$^2$ independently are
(a) C$_{1-6}$alkyl;
(b) C$_{1-6}$alkanoyl;
(c) CH$_2$OH;
(d) halo;
(e) C$_{1-6}$alkoxy;
(f) —NH$_2$;
(g) —NO$_2$;
(h) —COOH;
(i) —COOC$_{1-6}$alkyl; or (j) —H;

Particularly preferred are cyclosporin analogs wherein
R$^1$ is MeBmt or dihydro MeBmt;
R$^2$ is Abu;
R$^3$ is Sar or D-MeAla;
R$^4$ is MeLeu, MeVal, Me homo-Ala, or [Me-(a-methyl)Thr];
R$^9$ and R$^{10}$ are independently MeLeu or a fluorinated analog thereof;
R$^5$ is Val or a fluorinated analog thereof;
R$^6$ is MeAla, MeAbu, or a fluorinated analog thereof;
R$^7$ is Ala;
R$^8$ is D-Ala; and
R$^{11}$ is MeVal or a fluorinated analog thereof.

Fluorinated analogs represent the amino acid residues wherein one or more of the various C-H bonds in the side chain are replaced with C-F bonds. For example, fluorinated analog of Abu represents

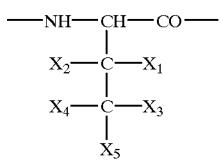

wherein $X_1$ to $X_5$ independently are H or F with the proviso that at least one of $X_1$, $X_2$, $X_3$, $X_4$, and $X_5$ is F.

Known derivatives and analogs of cyclosporins, which are known to be potent inhibitors of immunophilin rotamase activity and lack immunosuppressant effects include modified 6-position analogs, described by Dumont et al. (U.S. Pat. No. 4,914,188) and Durette (U.S. Pat. No. 5,236,899) and incorporated herein by reference. Other known non-immunosuppressive cyclosporin analogs include N-alkylated [Val]$^4$ derivatives, such as [MeVal]$^4$-CsA, disclosed by Fliri et al. (*Annal. N.Y. Acad. Sci* 696, 47, 1993), and incorporated herein by reference, and other derivatives with various side chain on the 4-position residue, as described by Papageorgiou et al. (BioMed. Chem. Lett. 1994, 2, 267–272) and incorporated herein by reference.

$K_i$ Test Procedure

Inhibition of the peptidyl-prolyl isomerase (rotamase) activity of cyclophilin by the inventive compounds can be evaluated by known methods described in the literature (Harrison and Stein, Biochemistry, 1990, 29, 3813–3816)., These values are obtained as apparent $K_i$'s and are presented for some of Examples 1–30 in Table I. The cis- trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values. The absorbance at 390 nm versus time is monitored for 90 sec using a spectrophotometer and the rate constants are determined from the absorbance versus. time data files.

The data for these experiments is presented in Table I.

TABLE I

| Example inhibition | Cyclosporin | Ki, cyclophilin |
| --- | --- | --- |
| 1 | CSA | 20 nM |
| 2 | dihydro-CsA | 100 nM |
| 3 | [dehydro-Ala]$^8$-CsA | 75 nM |
| 4 | [MeVal]$^4$-CsA | 10 nM |
| 5 | [Me-homoAla]$^4$-CsA | 24 nM |
| 6 | [Me-(a-methyl)Thr]$^4$-CsA | 18 nM |

Chick Dorsal Root Ganglion Cultures and Neurite Outgrowth

Dorsal root ganglia were dissected from chick embryos of ten day gestation. Whole ganglion explants were cultured on thin layer Matrigel-coated. 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% $CO_2$. Twenty-four hours later, the DRGs were treated with various concentrations of cyclosporin drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The data for these experiments are presented in Table II. Referring to FIG. 1 of the drawings, the $ED_{50}$ for cyclosporin A, the dose at which 50% of the maximal response was elicited, was obtained from dose-response curves (FIG. 1 is a typical example) and calculated to be 50 nM. The relative potencies of the other compounds in Table II are given relative to cyclosporin A, the number of "+" marks denoting the relative potency.

TABLE II

| Neurite Outgrowth in Chick DRG | |
| --- | --- |
| Example | Neurotrophic Potency |
| 1 | +++ |
| 2 | + |
| 3 | + |
| 4 | +++ |
| 5 | +++ |
| 6 | +++ |

The above data demonstrate that compounds which are inhibitors of cyclophilin's rotamase activity, whether immunosuppressive or non-immunosuppressive, are capable of promoting neurite outgrowth in cultured neurons, and are capable of achieving maximal effects comparable to nerve growth factor itself.

The invention being thus described; it will be obvious that the same may be varied in many ways. Such variations are not to be regarded as a departure from the spirit and scope of the invention and all such modifications are intended to be included within the scope of the following claims.

What is claimed is:

1. A method of effecting a neurological activity in an animal comprising administering an effective amount of a cyclophilin inhibitor compound, the cyclophilin inhibitor compound having an affinity for a cyclophilin-type immunophilin, wherein the cyclophilin-type immunophilin exhibits rotamase activity and the cyclophilin inhibitor compound inhibits the rotamase activity of the cyclophilin-type immunophilin with an apparent Ki of less than that of cyclosporin A.

2. The method of claim 1, wherein the neurological activity is selected from the group consisting of stimulating damaged neurons, promoting neuronal regeneration, promoting neuronal growth, augmenting neurite outgrowth, preventing neuronal degeneration, and treating a neurological disorder.

3. The method of claim 2, wherein the neurological disorder is selected from the group consisting of Alzheimer's disease, Parkinson's disease, neuropathies, peripheral neuropathies, trigeminal neuralgia, glossopharyngeal neuralgia, Bell's Palsy, myasthenia gravis, muscular dystrophy, progressive muscular atrophy, or traumatic injury to spinal, peripheral, or central nervous tissue.

4. A method of effecting a neurological activity in an animal comprising administering an effective amount of a non-immunosuppressive cyclophilin inhibitor compound, the cyclophilin inhibitor compound having an affinity for a cyclophilin-type immunophilin, wherein the cyclophilin-type immunophilin exhibits rotamase activity and the non-immunosuppressive cyclophilin inhibitor compound inhibits the rotamase activity of the cyclophilin-type immunophilin.

5. The method of claim 4, wherein the neurological activity is selected from the group consisting of stimulating damaged neurons, promoting neuronal regeneration, promoting neuronal growth, augmenting neurite outgrowth, preventing neuronal degeneration, and treating a neurological disorder.

6. The method of claim 5, wherein the neurological disorder is selected from the group consisting of Alzheimer's disease, Parkinson's disease, neuropathies, peripheral neuropathies, trigeminal neuralgia, glossopharyngeal neuralgia, Bell's Palsy, myasthenia gravis, muscular dystrophy, progressive muscular atrophy, or traumatic injury to spinal, peripheral, or central nervous tissue.

* * * * *